(12) United States Patent  
Gura et al.

(10) Patent No.: US 7,645,253 B2
(45) Date of Patent: Jan. 12, 2010

(54) WEARABLE ULTRAFILTRATION DEVICE

(75) Inventors: Victor Gura, Beverly Hills, CA (US); Edmond Rambod, Los Angeles, CA (US)

(73) Assignee: National Quality Care, Inc., Los Angeles, CA (US)

(*) Notice: Subject to any disclaimer, the term of this patent is extended or adjusted under 35 U.S.C. 154(b) by 234 days.

(21) Appl. No.: 10/846,618

(22) Filed: May 14, 2004

(65) Prior Publication Data

US 2004/0254514 A1 Dec. 16, 2004

Related U.S. Application Data

(63) Continuation-in-part of application No. 10/085,349, filed on Nov. 16, 2001, now Pat. No. 6,960,179.

(51) Int. Cl.
*A61M 37/00* (2006.01)
*C02F 1/44* (2006.01)

(52) U.S. Cl. ............ 604/5.04; 604/4.01; 604/5.01; 604/6.09; 604/6.11; 210/645; 210/646

(58) Field of Classification Search ............. 604/4.01, 604/5.01, 5.04, 6.09, 6.11, 29, 361, 358, 604/327; 210/645, 646, 739, 195.2, 433.1, 210/500.1; 422/44
See application file for complete search history.

(56) References Cited

U.S. PATENT DOCUMENTS

| 3,388,803 | A | | 6/1968 | Scott |
| 3,746,175 | A | | 7/1973 | Markley |
| 3,884,808 | A | * | 5/1975 | Scott .................. 210/109 |
| 3,989,622 | A | | 11/1976 | Marantz et al. |
| 3,994,799 | A | | 11/1976 | Yao et al. |
| 4,094,775 | A | * | 6/1978 | Mueller ................ 210/646 |
| 4,212,738 | A | | 7/1980 | Henne |
| 4,247,393 | A | | 1/1981 | Wallace |
| 4,267,040 | A | | 5/1981 | Schal |
| 4,269,708 | A | | 5/1981 | Bonomini et al. |
| 4,443,333 | A | | 4/1984 | Mahurkar |
| 4,563,170 | A | | 1/1986 | Aigner |
| 4,765,907 | A | | 8/1988 | Scott |
| 4,806,247 | A | * | 2/1989 | Schoendorfer et al. .. 210/321.68 |
| 4,897,189 | A | * | 1/1990 | Greenwood et al. ...... 210/195.2 |
| 4,968,422 | A | * | 11/1990 | Runge et al. ........... 210/321.69 |
| 4,997,570 | A | | 3/1991 | Polaschegg |
| 5,284,470 | A | | 2/1994 | Beltz |
| 5,360,445 | A | * | 11/1994 | Goldowsky ................ 623/3.22 |
| 5,391,143 | A | | 2/1995 | Kensey |

(Continued)

OTHER PUBLICATIONS

Martin Roberts, "Wearable Artificial Kidneys for Continuous Dialysis," ASAIO Journal, 1993, p. 19-23.

(Continued)

*Primary Examiner*—Leslie R Deak
(74) *Attorney, Agent, or Firm*—Howison & Arnott, L.L.P.

(57) ABSTRACT

An ultrafiltration device adapted to be worn on a portion of the body of a patient includes a blood inlet tube leading from a first blood vessel, a blood pump, an anticoagulant reservoir for infusing anticoagulants into the blood, a blood filter including a substrate through which the blood is circulated and filtered, a fluid bag for storing the excess fluid and a blood outlet tube leading to a second blood vessel.

19 Claims, 3 Drawing Sheets

U.S. PATENT DOCUMENTS

| | | | |
|---|---|---|---|
| 5,415,532 A * | 5/1995 | Loughnane et al. | 417/411 |
| 5,545,131 A | 8/1996 | Davankov | |
| 5,577,891 A | 11/1996 | Loughnane et al. | |
| 5,902,336 A | 5/1999 | Mishkin | |
| 5,944,684 A * | 8/1999 | Roberts et al. | 604/5.04 |
| 5,980,481 A | 11/1999 | Gorsuch | |
| 5,984,891 A | 11/1999 | Keilman et al. | |
| 6,117,100 A | 9/2000 | Powers et al. | |
| 6,117,122 A * | 9/2000 | Din et al. | 604/408 |
| 6,196,992 B1 | 3/2001 | Keilman et al. | |
| 6,332,985 B1 | 12/2001 | Sherman et al. | |
| 6,406,631 B1 | 6/2002 | Collins et al. | |
| 6,491,673 B1 * | 12/2002 | Palumbo et al. | 604/317 |
| 6,632,192 B2 | 10/2003 | Gorsuch et al. | |
| 6,685,664 B2 | 2/2004 | Levin et al. | |
| 6,796,955 B2 | 9/2004 | O'Mahony et al. | |
| 6,890,315 B1 * | 5/2005 | Levin et al. | 604/6.09 |
| 2002/0085951 A1 * | 7/2002 | Gelfand et al. | 422/44 |

OTHER PUBLICATIONS

A. Murisasco, et al; "Continuous Arterio-venous Hemofiltration in a Wearable Device to Treat End-stage Renal Disease," Trans Am Soc Artif Intern Organs, vol. XXXII, 1986, pp. 567.

A. Murisasco, et al, "A Continuous Hemofiltration System Using Sorbents for Hemofiltrate Regeneration," Clinical Nephrology, vol. 26, Supp. No. 1—1986, pp. S53-S57.

Arnold J. Lande', et al, "In Search of a 24 Hours Per Day Artificial Kidney," Journal of Dialysis, 1(8), 1977, pp. 805-823.

Shettigar, et al, "A portable hemodialysis/hemofiltration system independent of dialysate and infusion fluid." Artif Organs, vol. 7, No. 2, May 1983, pp. 254-256.

Manns, Markus et al, "The acu-men: A New Device for Continuous Renal Replacement Therapy in Acute Renal Failure," Kidney International, vol. 54, 1998, pp. 268-274.

Lockridge, R.S. Jr., "The Direction of End-Stage Renal Disease Reimbursement in the United States," Semin Dial, vol. 17, 2004, pp. 125-130.

Lockridge, R.S. Jr., et al, "Is HCFA's Reimbursement Policy Controlling Quality of Care for End-State Renal Disease Patients?" ASAIO J, vol. 47, 2001, pp. 466-468.

Manns, B.J. et al, "Dialysis Adequacy and Health Related Quality of Life in Hemodialysis Patients," ASAIO J, vol. 48, 2002, pp. 565-569.

Mapes, D.L. et al, "Health-related Quality of Life as a Predictor of Mortality and Hospitalization: The Dialysis Outcomes and Practice Patterns Study (DOPPS)," Kidney Int., vol. 64, 2003, pp. 339-349.

McFarlane, P.A. et al, "The Quality of Life and Cost Utility of Home Nocturnal and Conventional In-center Hemodialysis," Kidney Int., vol. 64, 2003, pp. 1004-1011.

Mohr, P. E., et al, "The Case for Daily Dialysis: Its Impact on Costs and Quality of Life," Am J Kidney Dis., vol. 37, 2001, pp. 777-789.

Patel, S. S., et al, "Psychosocial Variables, Quality of Life, and Religious Beliefs in ESRD Patients Treated with Hemodialysis," Am J Kidney Dis., vol. 40, 2002, pp. 1013-1022.

"Sorbent Dialysis Primer," Organon Teknika Corp., 1991.

Ronco, C., et al, "Blood and Dialysate Flow Distribution in Hollow-fiber Hemodialyzers Analyzed by Computerized Helical Scanning Technique," J Am Soc Nephrol, vol. 13, 2002, pp. S53-S61.

Mineshima, M., et al, "Effects of Internal Filtration on the Solute Removal Efficiency of a Dialyzer." ASAIO J, vol. 46, 2000, pp. 456-460.

Ronco, C., et al, "The Hemodialysis System: Basic Mechanisms of Water and Solute Transport in Extracorporeal Renal Replacement Therapies," Nephrol Dial Transplant, vol. 13 Suppl. 6, 1998, pp. 3-9.

Miwa, M. et al, "Push/Pull Hemodiafiltration: Technical Aspects and Clinical Effectiveness," Artif Organs, vol. 23, 1999, pp. 1123-1128.

Runge, T.M., et al, "Hemodialysis: Evidence of Enhanced Molecular Clearance and Ultrafiltration Volume By Using Pulsatile Flow," Int J Artif Organs, vol. 16, 1993, pp. 645-652.

Ding, L. H., et al, "Dynamic filtration of Blood: A New Concept For Enhancing Plasma Filtration," Int J Artif Organs, vol. 14, 1991, pp. 365-370.

Bird, R. B., et al, Transport Phenomena, Wiley, New York, 1976, pp. 126-130, 502-531, 558-563, 624-625, 700-711.

Welty, J. R., et al, "Chapter 27: Unsteady-state Molecular Diffusion," Fundamentals of Momentum, Heat, and Mass Transfer (2nd ed.), McGraw-Hill, New York, 1984.

Siaghy, E. M., et al, "Consequences of Static and Pulsatile on Transmembrane Exchanges During Vitro Microdialysis: Implication for Studies in Cardiac Physiology," Med Blot Eng Comput, vol. 37, 1999, pp. 196-201.

Utsunomiya, T., et al, "Effect of Direct Pulsatile Peritoneal Dialysis on Peritoneal Permeability and Lymphatic Absorption in the Rat," Nippon Jinzo Gakkai Shi, vol. 37, 1995, pp. 24-28.

Jaffrin, M. Y., et al, "Rationale of Filtration Enhancement in Membrane Plasmapheresis by Pulsatile Blood Flow," Life Support Systems, vol. 5, 1987, pp. 267-271.

Kobayashi, E., "A Study of Inorganic Ion Exchangers VII; The Synthesis of gammaNH4ZrH(PO4)2 And Ion-Exchange Properties of gamma-NH4Zr(HPO4)2.2H20," Bull Chem Soc Jpn, vol. 56, 1983, pp. 3756-3760.

Suri, R, et al, "Adequacy of Quotidian Hemodialysis," Am J Kidney Dis, vol. 42 Suppl. 1, 2003, pp. S42-S48.

Gotch, F. A., "The Current Place of Urea Kinetic Modelling with Respect to Different Dialysis Modalities," Nephrol Dial Transplant, vol. 13 Suppl. 6, 1998, pp. 10-14.

Gotch, F. A., et al, "Effective Diffusion Volume Flow Rates (Qe) for Urea, Creatinine, And Inorganic Phosphorous (Qeu, Qecr, QeiP) During Hemodialysis," Semin Dial, vol. 16, 2003, pp. 474-476.

Jaffrin, Michel Y., et al, "Simultaneous Convective and Diffusive Mass Transfers in a Hemodialyser," Transactions of the ASNE, May 1990, pp. 212-219, vol. 112.

Gura, Victor, et al, "Continuous Renal Replacement Therapy for End-Stage Renal Disease, The Wearable Artificial Kidney (WAK)," Cardiovascular Disorders in Hemodialysis, 2005, pp. 325-333, vol. 149.

Gura, Victor, et al, "Continuous Renal Replacement Therapy for Congestive Heart Failure: The Wearable Continuous Ultrafiltration System," ASAIO Journal 2006, pp. 59-61.

Murisasco, A., et al, "Continuous Arterio-venous Hemofiltration in a Wearable Device to Treat End-stage Renal Disease," Trans Am Soc Artif Intern Organs, 1986, Vol. XXXII, pp. 567-571.

Vermeulen Ph. D, Theodore, et al, "Adsorption and Ion Exchange," Perry's Chemical Engineers Handbook, 1984, Sixth Edition, Section 16, pp. 16-1-16-16.

Martin Roberts, "Wearable Artificial Kidneys for Continuous Dialysis," ASAIO Journal, 1993, p. 19-23.

A. Murisasco, et al., "A Continuous Hemofiltration System Using Sorbents for Hemofiltrate Regeneration," Clinical Nephrology, vol. 26, Supp. No. 1-1986, pp. S53-S57.

Arnold J. Landé, et al., "In Search of a 24 Hours Per Day Artificial Kidney," Journal of Dialysis, 1(8), 1977, pp. 805-823.

* cited by examiner

WEARABLE ULTRAFILTRATION DEVICE

REFERENCE TO RELATED APPLICATIONS

This application is a continuation-in-part of U.S. patent application Ser. No. 10/085,349, filed Nov. 16, 2001, now U.S. Pat. No. 6,960,179, issued Nov. 1, 2005, which is hereby incorporated by reference.

FIELD OF THE INVENTION

The present invention is directed to ultrafiltration devices, and more particularly to a portable ultrafiltration device that may be continuously worn by a patient.

BACKGROUND OF THE INVENTION

Fluid overload can be caused by many things including metabolic disease, renal failure and, especially, congestive heart failure (CHF), which has become a disease of epidemic proportions all over the globe. CHF is a progressive deterioration of the heart muscle that leads to an inability to pump enough blood to support the vital organs. Deterioration of the heart muscle leads to decreased pumping capacity and increased fluid retention caused by the lack of perfusion pressure of the kidneys due to the failure of the heart to pump enough blood at the proper pressure. Fluid overload can cause leg swelling, shortness of breath and water accumulation in the lungs, impairing the ability to properly breathe.

The incidence of class III and IV congestive heart failure (CHF) continues to grow along with the growing incidence of diabetes, obesity, coronary heart disease, Diastolic Dysfunction and other related ailments. In addition, the medically improved outcomes from Ischemic Heart Disease and Myocardial Infarction are generating an increased population of people suffering from varying degrees of CHF.

Treating patients with CHF is presently one of the major expenses in the healthcare bill of any westernized nation. Furthermore, treating patients with CHF is one of the most significant causes of financial loss in the U.S. hospital industry.

Removal of excess fluids from the body can be accomplished with diuretics and other drugs that improve the performance of the heart muscle.

Thanks to numerous pharmacological agents such as ACE inhibitors, diuretics and beta blockers, the morbidity and mortality of CHF has become somewhat improved. Pacemakers and implantable defibrillators have aided in this regarding also.

Regardless of the advancements in medical technology some of the major patient problems associated with CHF are fluid overload and sodium retention. Both fluid overload and sodium retention are associated with various endocrine derangements and release noxious cytokines that may further aggravate the CHF condition. These drugs become gradually ineffective over time and may also cause undesirable effects such as kidney failure.

There is a growing body of literature supporting the conclusion that the physical removal of fluid by convection (i.e., ultrafiltration) of blood can significantly improve patient outcomes and shorten hospital stays and intensive care unit utilization. Fluid removal may be superior to the administration of very large losses of diuretic drugs.

Advantages of ultrafiltration over diuretic drugs include: (1) efficient fluid removal without side effects such as kidney failure and blood pressure drops; (2) prompt relief from shortness of breath and swelling; and (3) improvement regarding certain adverse hormonal effects that are associated with CHF.

Ultrafiltration is performed by pumping blood from a catheter in an artery or a large vein, though a blood filter or a dialyzer while creating a gradient of pressure through the filter membrane. The pressure gradient forces the passage of fluid out of the blood by convection and the fluid is drained out.

Conventional ultrafiltration devices suffer from several drawbacks. Usually, these devices are cumbersome, heavy and must be hooked to electrical outlets for power. Since ultrafiltration patients must remain connected to these devices for many hours, their ability to perform normal every day activities is severely limited. In addition, typical ultrafiltration treatments are geared for fast removal of several liters of excess fluid. However, the fluid removal is only temporary and the excess fluid usually reaccumulates in the patient's body after a short period of time. The reaccumulation of fluid is harmful to the patients, as the kidneys are further injured by the progress of CHF and the side effects of the diuretic drugs used to treat the heart.

Presently ultrafiltration devices are not designed to economically provide a single patient prolonged or continuous ultrafiltration. In addition, acute treatments performed over 4 to 6 hours of hemofiltration on a patient, can be efficient and capable of removing up to around 23 liters of excess fluid from a patient in one session, but are not physiologically good for the patient and can be conducive of blunt shifts in fluid content in various compartments of a patient's body. Such large amounts of fluid removal may also create hypotension and hemodynamic instability. Furthermore, the present ultrafiltration methods do not provide for a steady removal of excess fluids and sodium from the patient's body.

A further problem with ultrafiltration devices is that repeated reconnection to an ultrafiltration device requires accessing blood flow by puncturing a large blood vessel and forming an arteriovenous shunt. These shunts only last for limited periods of time and are subject to infection, clotting and other complications that result in numerous hospitalizations and repeated surgical interventions. Similar problems also exist when a patient's blood stream is accessed by alternative methods, such as by inserting large catheters into large veins and arteries.

In view of the above disadvantages, there is a substantial need for a portable ultrafiltration device that provides continual, steady and smooth removal of excess fluid from the body.

SUMMARY OF THE INVENTION

Embodiments of the present invention alleviate to a great extent the above-noted and other disadvantages by providing a portable, completely wearable ultrafiltration device that performs continuous, steady and smooth removal of excess fluid from the body. Importantly, an exemplary ultrafiltration device does not require a patient to be hooked up to a large machine for many hours a day, several days per week. Instead, an exemplary ultrafiltration device can conveniently be worn on a patient's body for continual use, 24 hours a day, seven days a week, providing steady and smooth removal of excess fluid from the body and preventing the shortness of breath and swelling that are associated with CHF.

One aspect of embodiments of the present invention involves an ultrafiltration device adapted to be completely worn on a portion of the body of a patient, including a blood pump and a blood filter for separating excess fluid from the blood.

A further aspect an exemplary ultrafiltration device is that the device is in the form of a belt adapted to be worn about the waist, shoulder, thigh or other body portion of a patient, wherein the belt includes a pair of end portions which are secured together by a belt fastening means.

Another aspect of an embodiment of the present invention involves an ultrafiltration device adapted to be completely worn on a portion of the body of a patient includes a blood inlet tube leading from a first blood vessel, a blood pump, an anticoagulant reservoir from which anticoagulants are infused into the blood, a blood filter including a substrate through which the blood is circulated and filtered, a fluid bag for storing the excess fluid and a blood outlet tube leading to a second blood vessel.

These and other features and advantages of embodiments of the present invention will be appreciated from review of the following detailed description of the invention, along with the accompanying figures in which like reference numerals refer to like parts throughout.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE PREFERRED EMBODIMENTS

Ultrafiltration is a process by which excess fluid in the form of water is removed from the blood, wherein the excess fluid in the blood is moved from one side of a filtering device to another. The filtering device contains many hollow fibers made out of a semipermeable membrane. While blood flows inside of the hollow fibers, water and fluid from the blood moves through the membrane wall and is drained off. The purified blood remains inside the hollow fibers and is returned to the body.

Figure 1:
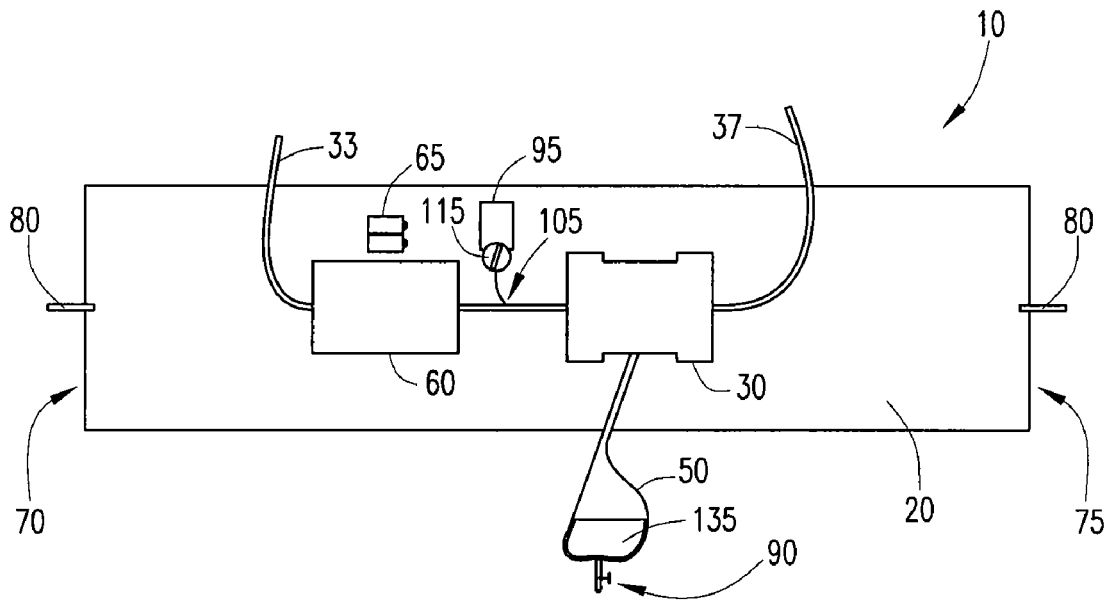
FIG. 1 is a perspective view of an embodiment of an assembly in accordance with the present invention.

Referring to FIG. 1, an ultrafiltration device 10 is designed to extract a targeted volume of fluid from the blood of a patient at a precisely controlled rate. The ability to predictably remove excess fluid from the blood reduces the risk of removing too much fluid too quickly, which can result in low blood pressure and vital organ damage.

The ultrafiltration device 10 comprises a belt 20 adapted to be worn about a portion of the body of the patient. According to some embodiments, the ultrafiltration device 10 is adapted to be worn about the waist of the patient. However, as would be understood to those of ordinary skill in the art, the device 10 may also be worn about other portions of the patient's body, such as over a shoulder or around a thigh. According to some embodiments, the weight of the belt 30 is less than two pounds.

As seen in FIG. 1, the belt 20 includes a pair of end portions 70, 75, which are secured together by a belt fastening means 80 such as a buckle 80, snaps 80, buttons 80 or hook and loop fasteners 80. The belt 20 further includes a blood filter 30 including a blood inlet tube 33 leading from a first blood vessel and a blood outlet tube 37 leading to a second blood vessel in the patient. The belt 20 also includes a blood pump 60, which forces the patient's blood through the filter 30. The pump 60 may be a shuttle pump, piston pump, roller pump, centrifuge pump, piezoelectric pump, or other convention pump. Convention power sources 65 such as batteries 65 can be use to power the blood pump 60.

The blood filter 30 separates excess fluid from the patient's blood. The excess fluid is drained in to an excess fluid bag 50, which is to be periodically emptied via tap 90. The fluid bag 50 can be positioned in the vicinity of a thigh, a leg, an ankle, an arm, or any other suitable body portion of the patient.

The coagulation of the blood circulating through the device 10 is prevented by the constant infusion of anticoagulant, which is infused from an anticoagulant reservoir 95 through a port 105 and into the blood inlet tube 33. In some embodiments, anticoagulant is infused using a battery powered anticoagulant pump 115. The pump 115 maybe a shuttle pump, piston pump, roller pump, centrifuge pump, piezoelectric pump, or other convention pump. Typical anticoagulants are infused into the blood 150 include, but are not limited to, heparin, prostacyclin, low molecular weight heparin, hirudin and sodium citrate. According to other embodiments, blood clotting inside the device 10 can be prevented by the oral administration of anticoagulent drugs including, but not limited to, coumadin.

Figure 2:
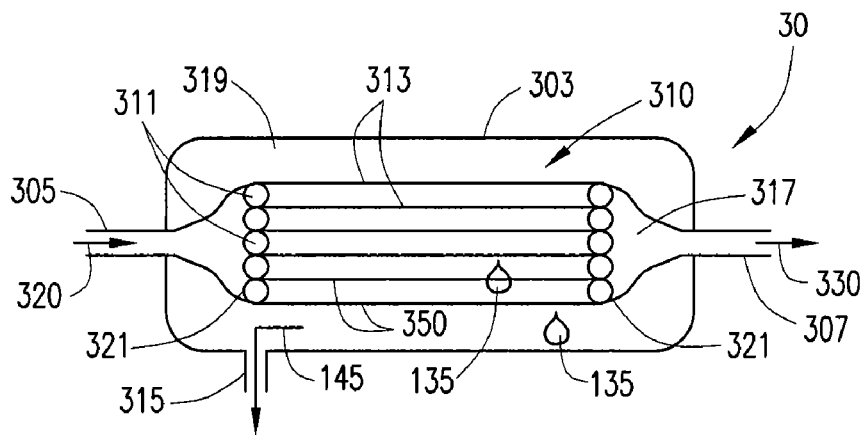
FIG. 2 is a perspective view of an embodiment of an assembly in accordance with the present invention.

Referring to FIG. 2, according to some embodiments, the blood filter 30 is a conventional blood filter 30 comprising a plurality of hollow fibers 310 having fixed, i.e., non-moving ends 321 through which the blood 150 flows. Blood filter 30 includes a housing 303, blood inlet 305, a blood outlet 307 and a fluid outlet 315. The exterior walls 350 of the hollow fibers 310 are semiporous so that excess fluid 135 in the form of water 135 and impurities 135 can be removed from the blood 150. As illustrated, each of fibers 310 a first, interior surface 311 in contact with blood 150 and a second, exterior surface 313 where excess fluid 135 is received. Blood inlet 305, interior surfaces 311 of fibers 310 and blood outlet 307 define a blood side 317 of filter 30. Housing 303 and exterior surfaces 313 of fibers 310 define a fluid side 319 of filter 30 where excess fluid 135 from blood 150 is received. As illustrated, blood side 317 of filter 30 is separated from fluid side 319 of the filter by fibers 310. In the illustrated embodiment, fluid side 319 of filter 30 is enclosed except for fluid outlet 315 such that the only fluid on fluid side 319 of filter 30 is fluid separated from blood 150 and the only flow though fluid side 319 is excess fluid filtered from blood 150 that exits filter 30 though fluid outlet 315. As indicated by arrows 320, 330, excess fluid 135 is drained from the hollow fibers 310, which act as a sieve such that excess fluid 135 passes through, but not blood 150. The excess fluid 135 is drained out of the filter 30 through fluid outlet 315 in a direction indicated by arrow 145.

The blood 150 moves through the hollow fibers 310 under pressure from the blood pump 60. This pressure causes the excess fluid 135 in the blood 150 to filter out through the fiber pores, into the other side of the hollow fibers 310, from where the excess fluid 135 is drained out to the fluid bag 50. The magnitude of pressure within the fibers 310 determines the amount of net excess fluid 135 movement removed through exterior walls 350. Small particles within the blood 150 are also removed during this process, but particles larger than the blood filter pore size will be left behind in the blood 150.

Figure 3:
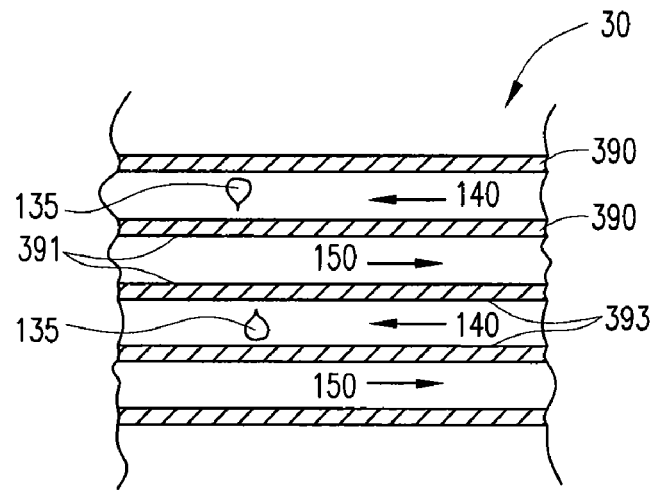
FIG. 3 is a perspective view of an embodiment of an assembly in accordance with the present invention.

Referring to FIG. 3, according to other embodiments, the blood filter 30 is an alternative conventional blood filter 30 comprising a plurality of parallel sheets 390 of semiporous material, wherein air 140 is circulated on one side of the parallel sheets 390 and the blood 150 circulates in the opposite direction on the other side of the parallel sheets 390. As illustrated, each of sheets 390 has a first surface 391 in contact with blood 150 and a second surface 393 where excess fluid 135 is received. The blood filters 30 of these embodiments are conventional and well known in the art. Excess fluid 135 and small particles are removed from the blood 150 through parallel sheets and drained off into excess fluid bag 50.

Figure 4:
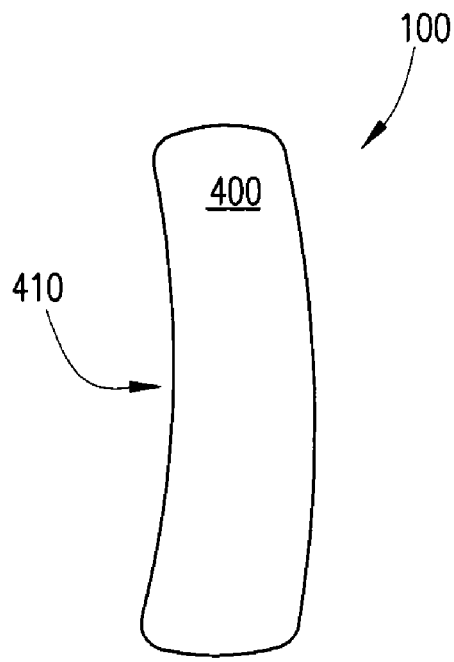
FIG. 4 is a perspective view of an embodiment of an assembly in accordance with the present invention.

Referring to FIG. 4, according to some embodiments, the blood filter 50 has a flexible casing 400 adapted to conform to the body contour of the patient. In addition, the body-side wall 410 of each casing 400 is concave to further correspond to bodily curves of the user. The casing 400 can be made of any suitable material having adequate flexibility for conformance to the portion of the body to which it is applied. Suitable materials include, but are not limited to polyurethane and poly vinyl chloride.

Figure 5:
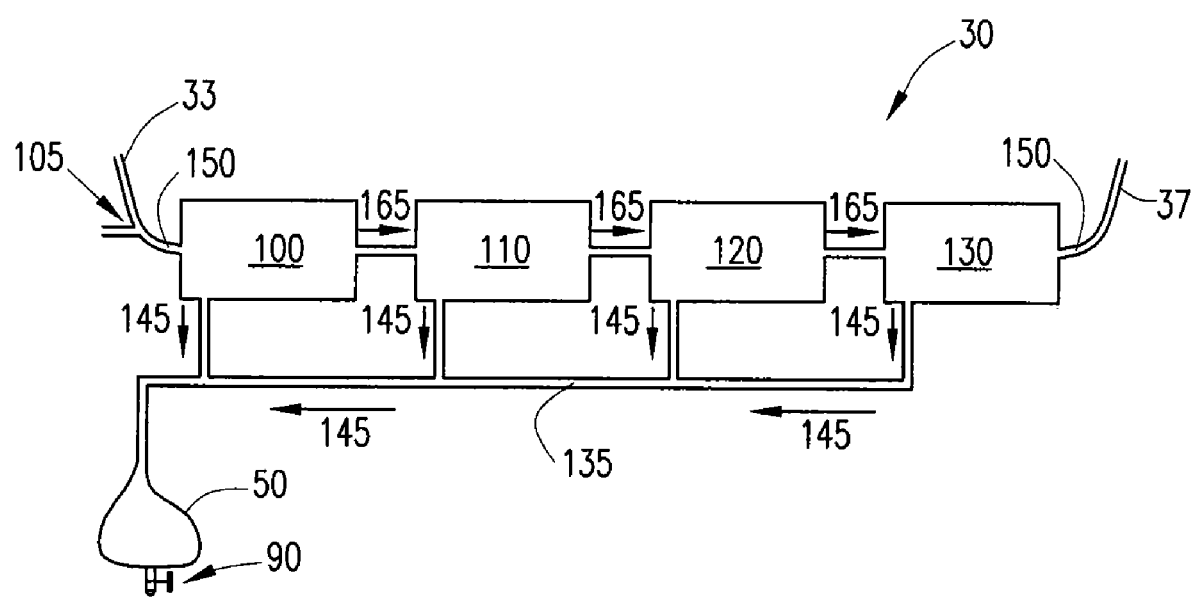
FIG. 5 is a perspective view of an embodiment of an assembly in accordance with the present invention.

Referring to FIG. 5, in an alternative embodiment, the blood filter 30 includes a plurality of miniaturized blood filters 100, 110, 120, 130 that remove impurities from the blood 150 of the patient. The number of filters, 110, 120, 130 in the plurality of filters, 110, 120, 130 may be varied to reflect different ultrafiltration prescriptions. The plurality of blood filters 100, 110, 120, 130 are connected in series, whereby the blood pump 60 forces the patient's blood 150, in a first direction, through the filters 100, 110, 120, 130, as indicated by arrows 165. Excess fluid 135 is drained from the blood filters 100, 110, 120, 130 and into the excess fluid bag 50 as indicated by arrows 145. As would be understood by those of ordinary skill in the art, the filters 100, 110, 120, 130 can also be connected in parallel without departing from the scope of the invention.

Figure 6:
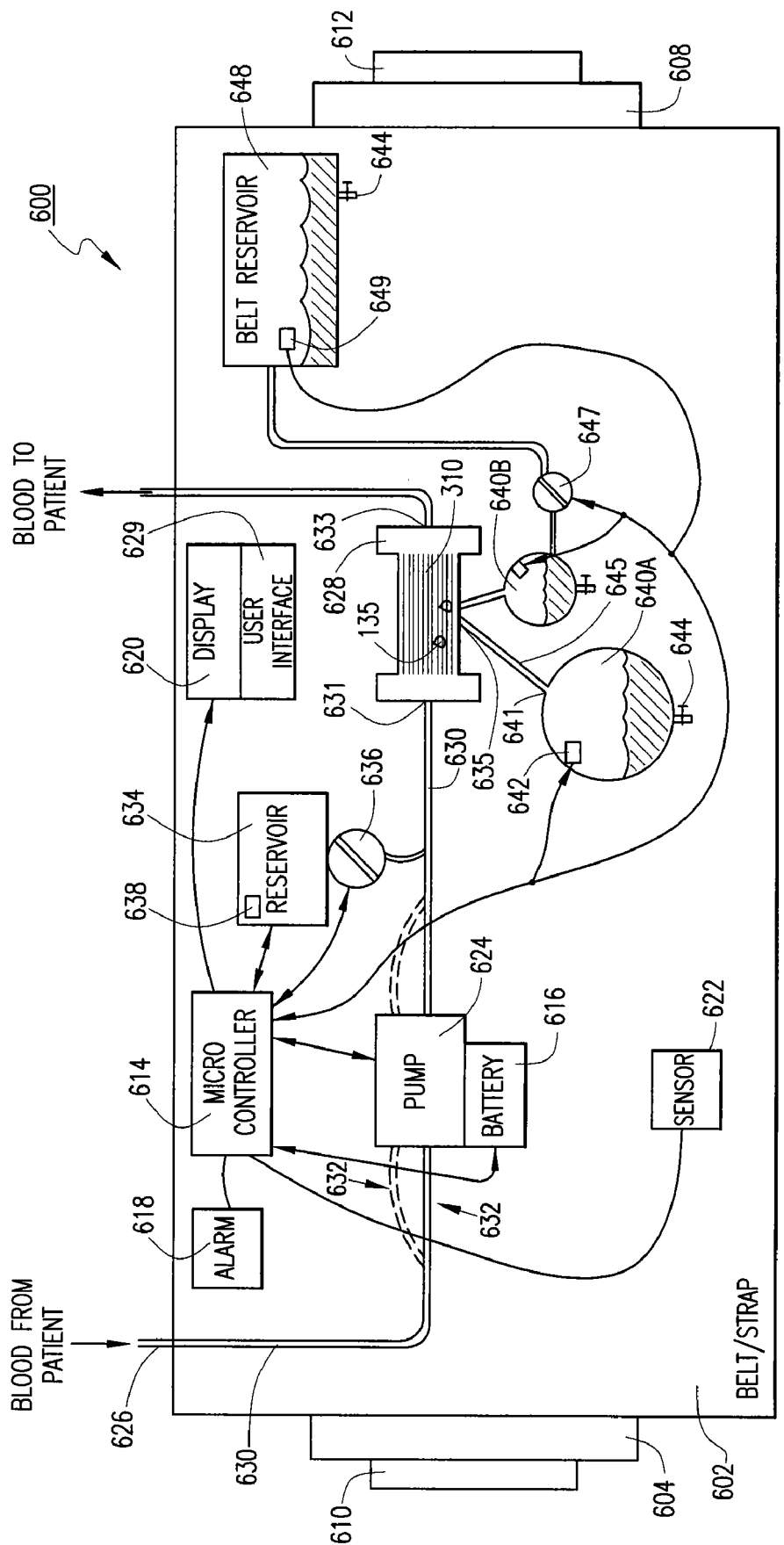
FIG. 6 is a diagram of a wearable ultrafiltration device in accordance with an embodiment of the invention.

Referring now to FIG. 6, another exemplary embodiment of the present wearable ultrafiltration device 600 is depicted. The wearable ultrafiltration device 600 is built into or is part of a patient wearable belt or strap 602. The belt 602 includes at least a pair of end portions 604, 608 that are secured together by a fastening means (not specifically shown) 610, 612 that could be any number of fastening devices suitable to secure the ends of a belt or strap together including, but not limited to snaps, buttons, buckles, laces, hoods and loops, zippers, etc.

A microcontroller 614 is utilized to control and monitor various aspects of the exemplary wearable ultrafiltration device. The microcontroller 614 is preferably a very low power microcontroller, but may be substantially any microcontroller adapted to operate in the ultrafiltration device. The microcontroller monitors the battery 616 or other acceptable power sources. The battery 616 is removably installed in the ultrafiltration device. The battery may also be recharged while remaining in the device via a battery charger device connected to the wearable ultrafiltration device. Preferably the battery is rechargeable and can provide enough energy to the wearable ultrafiltration device 600 for at least 6 or more hours of continuous, uninterrupted device operation. The microcontroller by itself or via another circuit monitors the energy status of the battery 616. If the microcontroller 614 determines that the battery is running low on energy or has less than an estimated predetermined amount of time left in its energy reserves, the microcontroller 614 may trigger an alarm condition via alarm circuit 618 which may provide any one or more of an audio, visual, or physical alarm signal. The physical alarm signal may include vibrations or small tingle-style shocks providing the patient an alarm indication that can be felt. An alarm condition or warning condition may be displayed on the display 620 using a liquid crystal, light emitting diode or other display technology. An alarm condition may also turn off an exemplary wearable ultrafiltration device 600.

A moisture sensor 622 is in communication with the microcontroller 614. The moisture sensor 622 is used to detect condensation or liquid present inside the packaging or covering over (not specifically shown) the wearable ultrafiltration device 600. The packaging or covering may be a plastic, cloth, rubberized material or other suitable material. The covering may cover a portion of the ultrafiltration and allow access to the various parts of the exemplary device.

Condensation or the presence of liquid inside the packaging or outer cover of an exemplary ultrafiltration device may be indicative of patient blood leakage or other fluid leakage. Upon sensing moisture, the moisture sensor 622 provides a signal to the microcontroller 614 and an alarm is sounded via the alarm circuit 618. Furthermore, the pump 624 may be turned off by the microcontroller 614 to help minimize potential blood loss.

The pump 624 is an electric pump. Blood from the patient is extracted via a blood inlet tube 626. The pump 624 pumps the blood to and through the blood filter 628. The pump 624 is preferably powered via a rechargeable battery pack 616. The microcontroller may actively adjust various pumping variables. Potential adjustable pump variables include adjusting the torque of the pump motor, the pumping rate (i.e., strokes or pump cycles per minute), the pressure of the blood between the main pump 624 and the blood filter 628.

The presently preferred pump is a single channel pulsatile pump. In general, a pulsatile pump has a rubberized cartridge with an input valve at the input end of the cartridge and an output valve at the output end of the cartridge. The motor within the pump presses the rubberized, tubular portion of the cartridge. The pressing squeezes and evacuates the contents of the cartridge out the open end output valve. As the pump motor spins and causes the mechanics of the pump to release pressure from the rubberized portion of the cartridge, the output valve closes and the input valve allows fluid (blood) to enter the cartridge only to be squeezed out the output valve in the next pump cycle. The input and output valves are one-way valves allowing flow in a single direction. An exemplary pump can provide a blood flow rate of about 15 to 100 ml/min (pulsatile). The approximate dimensions of the pump 624 are about 9.7×7.1×4.6 cm with a weight of less than 400 grams. An exemplary pulsatile pump uses, preferably, less than 10 watts of energy. The exemplary pump can provide low battery power and occlusion alarm signals to the microcontroller 614.

To potentially decrease the overall energy requirement of pump 624, a dual channel pulsatile style pump can be incorporated into an exemplary wearable ultrafiltration device as depicted by the dotted lines in FIG. 6. The blood circuit tubing 630 split into two parallel blood routes 632 before the blood pump 624 and the blood is pumped through the exemplary pulsatile style pump in parallel. After exiting the pulsatile pump the two parallel blood routes are recombined into a single blood route 630. By using a dual channel pulsatile pump, the pump can operate at about half the rate as a single channel pulsatile pump and move the same amount of blood. A dual channel pulsatile pump could also move blood through the exemplary wearable ultrafiltration device 600 at an estimated maximum rate of about 200 ml/min or more depending on the size of the chambers of the maximum speed of the pump. The maximum rate can be utilized to decrease the fluid content of the patient's blood quickly in circumstances when the exemplary wearable ultrafiltration device is first turned on after being turned off for an extended period of time.

Ideally, the dual chamber pulsatile pump configuration would pump each of the two chambers at about 180° out of phase to smooth out the blood flow rate.

Other types of blood pumps 624 can be successfully incorporated into embodiments of the wearable ultrafiltration device. Such other types of pumps include, but are not limited to, a shuttle pump, a piston pump, a roller pump, a centrifuge pump, a piezoelectric pump, or other conventional pumps. Whatever pump is utilized, the pump 624 ideally has a manually or electrically adjusted flow rate from about 20 ml/min to about 120 ml/min. As discussed, the main pump 624 may be controllable manually by the user, physician or by microcontroller 614 control.

The microcontroller 614 may display pump status or other status information on the display 620. User interface controls 634, buttons, switches, slide controls, knobs, connectors, infrared received etc. (not specifically shown) may be used to enable a patient, physician, nurse or other computer device to adjust various settings and controls on an exemplary ultrafiltration device 600. For example, the pump 624 pumping rate, torque, valve opening size, flow rate, rpm, and on/off, may all be monitored or controlled via the user interface 632 or other device external to the exemplary ultrafiltration device 600.

After the blood passes through the main pump 624, it continues on the blood circuit 630. A reservoir 634 for containing a blood thinner or anticoagulant is part of an ultrafiltration device. A micropump 636 provides the fluid contents of the reservoir 634 in a measured continuous or non-continuous manner to the blood circuit 630 prior to the blood filter 628. A micropump 636 is a type of pump that can pump microscopic or miniscule amounts of fluid each minute. A micropump 636 may pump a fluid in the range of 0.1 to 400 ml/hr (milliliters per hour) and requires from about 1 to 500 milliwatts to operate. There, at present, are various types of micropumps including, but not limited to a piezoelectric pump, a solenoid pump, micro-piston pump, peristaltic pump, nanotechnology pump, microtechnology/micromachined pump, syringe pump, roller pump, centrifuge pump, or diaphragm pump.

The blood thinner and/or anticoagulant may be mixed with the blood at point in the blood circuit between the blood inlet tube 626 and the blood filter 628.

Also in the reservoir 634, a level sensor 638 senses the amount of fluid therein. The level sensor 638 is in electrical communication with the microcontroller 614. The microcontroller sends an alarm signal to the alarm 618 if the fluid level in the reservoir 634 is below a first predetermined level or volume. The microcontroller 614 may also turn the ultrafiltration device 600 off if the fluid level in the reservoir 634 is below a second predetermined level or volume. The second predetermined level being equal to or less than the first predetermined level.

The combination of reservoir 634 and micropump 636 infuse the blood thinner or anticoagulant into the blood flowing in the blood circuit 630. Presently preferred blood thinners or anticoagulants include, but are not limited to, heparin, prostacylin, low molecular weight heparin, hirudin and sodium citrate. The anticoagulant is infused into the blood prior to the blood filter 628 and in some embodiments prior to the main pump 624 in order to help minimize the potential of blood clots in the blood filter 628 and perhaps the main pump 624.

The blood filter 628, like the previously discussed blood filter 30, may be a specially sized blood filter that uses conventional technology. As illustrated, blood filter 628 includes a blood inlet 631, a blood outlet 633 and a fluid outlet 635. Fluid outlet 635 is connected directly to fluid inlet 641 of fluid bladder 640A by means of tube or fluid conduit 645. The exemplary blood filter 628 comprises a plurality of hollow fibers 310 that are semipourous enough to allow fluids in the form of water and impurities to be removed from the patient's blood without allowing blood cells to be removed from the blood. The hollow fibers act as a sieve such that some excess fluid passes through the semipourous walls of the fibers without allowing blood cells to pass.

Still referring to FIG. 6, the fluids 135 filtered from the blood in the blood filter 628 are captured in a fluid bladder 640A or fluid bag. The fluid bladder 640A may hang below the belt 602 (not specifically shown) and be able to store from about 0.1 to about 2 liters of fluid. A sensor 642 is connected to the microcontroller 614 to enable an alarm 618 to sound when the fluid bladder 640A is filled to a predetermined level. Furthermore, the microcontroller 614 may turn an exemplary wearable ultrafiltration device off when the level sensor 642 indicates that the fluid bladder 640A is full or has a predetermined amount of fluid therein.

The fluid bladder 640A may contain an absorbent material (not specifically shown) for absorbing fluid that is deposited in the fluid bladder 640A. The absorbent material may be a cotton, polymerer, dried sponge, compressed material, powder, jell, or other absorbent material. The absorbent material may perform one or more functions including, but not limited to, limiting the movement or "sloshing" of the fluid in the bladder, to expanding the bladder so the patient will know that the bladder is full, to expand the fluid bladder so that it exerts pressure or weight against a microswitch (not specifically shown). The microswitch may be used to provide a signal to the microcontroller that indicates the fluid bladder is full, to create a conductive or ionic source to enable a moisture sensor or fullness sensor to operate and provide a fluid bladder fullness signal to the microcontroller.

Fluid bladder 640A may have a means for emptying the fluid bladder thereon in the form of a manual or electro mechanical valve. In an embodiment a valve 644 may be opened to drain the fluid from the fluid bladder 640A. In another embodiment, the fluid bladder 644 is detachable and disposable.

In another embodiment of the wearable ultrafiltration device 600, a small reservoir 640B is either part of or connected to the blood filter 628. A small pump or micropump 647 transfers the filtered fluids from the small reservoir 640B into a belt mounted container or reservoir 648. The small pump or micropump 647 may also provide vacuum pressure or negative pressure to the blood filter 628 thereby potentially increasing the filtering effect and the rate of fluid removal from the blood. The small or micropump 647 may also be used to eliminate the fluid bladder 640B by pumping fluids directly to fluid container 648. The fluid container 648 may comprise a fullness or fluid level sensor 649. The fullness sensor 649 may be a microswitch or pressure sensitive senor that senses a fullness of a bladder (not specifically shown) inside the belt reservoir 648. As the bladder, within the belt reservoir 648 fills, the bladder presses against the fullness sensor 649 and a fullness signal is received by the microprocessor. A material or device that expands when it absorbs or is in the presence of fluid may be contained within the belt reservoir 648. The material or device within the belt reservoir 648 may be a bladder, cotton, pressed sponge-like material, an absorbent powder or pellet substance that expands, absorbs or becomes thick or jell-like when wet. Absorbent material within the belt reservoir 648 may also minimize or eliminate a sloshing of any fluid contained therein. The belt mounted fluid reservoir 648 eliminates a need for a hanging bag or bladder to collect waste fluids. The belt mounted fluid reservoir may be easily attached and detached from an exemplary ultrafiltration device 600 for emptying by the patient.

As the blood flows through the blood circuit 630, excess fluid and blood contaminants are separated from the blood via ultrafiltration at the blood filter. The excess fluid 135 is removed from the blood filter 628 as it sweats or percolates through the walls of the hollow fibers 310. It is understood that various types of blood filters or dialyzer devices may be used in an exemplary embodiment.

Since embodiment of the present ultrafiltration device is intended to be worn by a patient on or as part of a waist self or shoulder harness/strap, it is somewhat important for an exemplary ultrafiltration device to function regardless the ultrafiltration device's relative orientation with respect to being horizontal with the ground. In other words, an exemplary ultrafiltration device should be operational regardless of whether the patient wearing the device is standing, sitting, lying down, or upside down. Thus, embodiments of the present ultrafiltration device operates in any three-dimensional orientation so that the device will operate twenty-four hours a day regardless whether the patient is standing, sitting or lying down.

Other embodiments of the present invention may have a sensor that determines whether ultrafiltration device is an operational orientation. If the ultrafiltration device is not in an orientation wherein it will operate properly, then the sensor will turn off or shut down the pumps via a switch or microprocessor control.

An exemplary ultrafiltration device is light enough to be completely wearable by a patient. An exemplary ultrafiltration device weighs between one and five pounds (with or without fluids).

Various experiments were performed with an exemplary ultrafiltration device. The exemplary ultrafiltration device was being used to treat fluid overload. Animals, in particular, six pigs, were used to test an exemplary ultrafiltration device. Each pig underwent bilateral urethral ligation to produce acute renal failure and fluid overload. After 24 to 48 hours each animal was anesthetized and a double lumen catheter was inserted in their jugular vein. The cartoid artery was canulated for blood sampling.

The double lumen catheter was connected to the exemplary device and the blood was ultrafiltered. The device consisted of a hollow fiber dialyzer and a port for heparin infusion. Heparin was administered into the blood circuit regularly to prevent the clotting of blood in the device. A battery-operated pulsatile pump (FIG. 1) propelled the blood through the device. The total weight of the pump and the hollow fiber dialyzer was less than 2.5 lbs. The design of the device used in the test is shown in FIG. 1.

The general results of the experiments are as follows:

The blood flow rates through the device ranged between 0 and 200 ml per min.

The average blood flow was about 44 ml/min.

The amounts of fluid removed from each animal (ultra filtration) by the device ranged from 0 to 700 ml/hour and is tabulated in Table I.

The amount of fluid removal was manually adjusted by partially or completely occluding the exit of the ultrafiltrate to the collection bag. Again, the hourly amount of fluid removed ranged from 0- to 700-ml/hr.

There were no complications or untoward effects on the animals attributable to the ultrafiltration during the experiments.

TABLE I

Amount of fluid removed (in ml.) from each animal in eight hours. The last row depicts the average hourly rate of ultrafiltration.

| | Pig C (g) | Pig D (g) | Pig E (g) | Pig F (g) | Pig G (g) | Pig H (g) |
|---|---|---|---|---|---|---|
| 1 hr | 400 | 100 | 100 | 100 | 150 | 180 |
| 2 hrs | 700 | 200 | 200 | 200 | 220 | 200 |
| 3 hrs | | 300 | 200 | 300 | 380 | 350 |
| 4 hrs | 800 | 400 | 250 | 400 | 500 | 700 |
| 5 hrs | | 500 | 300 | 500 | 600 | 710 |
| 6 hrs | | 500 | 500 | 800 | 680 | 1410 |
| 7 hrs | | 620 | 600 | 1000 | 700 | 1400 |
| 8 hrs | | 800 | 1000 | 1150 | 800 | 1400 |
| Average | 100 | 100 | 125 | 144 | 100 | 175 |

The results of the experiment merits additional discussion because of the successful controlled removal of fluid from the pigs blood. There is a growing notion and body of literature supporting the hypothesis that blood ultrafiltration is an effective tool in the treatment of class III and IV CHF patients. There seems to be significant effects on the electrolyte and endocrine derangements associated with this condition as well as an avoidance of diuretics that are so often conducive to renal failure, hypotension and further metabolic complications. However, this presently can only be accomplished by using a dialysis machine or other ultrafiltration device that is not amenable to be used substantially continuously while a patient is ambulatory. The aim of the present experiments was to evaluate the efficiency and actual fluid removal with an exemplary miniaturized ultrafiltration device.

The exemplary ultrafiltration device operated very well in terms of removal of plasma ultrafiltration at a wide range of flow rates and volumes. Fluids were removed from the blood at rates ranging from 0 to 700 ml/hr without difficulty, except for a decrease in blood flow through the exemplary ultrafiltration device as fluid removal was increased beyond about 700 ml/hr. It is believed the difficulty is attributable to the marked hemoconcentration inside the hollow fibers of the blood filter as a consequence of removing too much water. Decreasing the rate of ultrafiltration resulted in a return of the blood flow to the previous rate. Another possible technique for maintaining ample blood flow with a high ultrafiltration rate is to utilize a blood filter having hollow fibers or lumens with a larger inner diameter, for example up to 1 mm in diameter or utilizing a different shaped lumen for example, one having an oval or oblong cross-section having a larger cross-sectional area.

The exemplary ultrafiltration device proved effective at removing large quantities of water from a patient at virtually any rate a treating physician might desire. As a result an exemplary wearable ultrafiltration device may be valuable for the treatment of fluid overload, specifically in CHF patients.

Using a blood flow in the range of 10 to 70 ml/min, and preferably around 44 ml/min, make it unlikely that patients may experience blunt compartment shifts or hemodynamic compromise in otherwise very ill patients.

An exemplary wearable ultrafiltration device can, unlike other already existing ultrafiltration devices, be completely worn and be operational for treating a patient by ultrafiltration 24 hours a day, seven days a week in a substantially continuous manner. The treatment can be applied in a hospital or in an ambulatory condition.

An exemplary wearable ultrafiltrate device can be used to effectively reduce a patient's incidence of acute pulmonary edema, ascites, and other stigmata of class III and IV CHF.

An additional aspect of an embodiment of the present wearable ultrafiltration device is that a patient who utilizes the device may be able to significantly reduce their usage of diuretics and other CHF related drugs. Embodiments of the present invention are also effective at removing sodium along with fluids. Since sodium retention is one of the problems related with CHF, CHF patients are usually condemned to draconian restrictions of salt intake, commonly 2 to 3 grams per day. On the other hand, the sodium concentration in the ultrafiltrate produced by an embodiment of the present device is equal to the concentration in the blood plasmas (i.e., about 0.9 grams of salt per 100 ml). Thus, steady removal about 1.5 to 2 liters of ultrafiltrate from a patient each day results in the removal of about 13.5 to 18 grams of salt or sodium per day from the patient. This result would not only eliminate or reduce a patient's salt restriction and the need for diuretics and other drugs, but also may result in having to encourage the patient to eat foods with more salt. The impact of an exemplary device on a patient's quality of life by reducing CHF related shortness of breath, leg swelling and ability to enjoy salt in their food will be significantly positive, but difficult to quantify.

It is expected that outcomes in the treatment of CHF patients, namely a significant reduction in morbidity and mortality will be significant, but further clinical studies are needed to quantify these potential results. Embodiments of the present invention may provide economic impacts by reducing the length of patient hospital stays, ICU needs and drug consumption. The overall economic impact and value remains to be studied.

Thus, it is seen that a wearable ultrafiltration device is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

The previous description is of a preferred embodiment for implementing the invention, and the scope of the invention should not necessarily be limited by this description. The scope of the present invention is instead defined by the following claims.

What is claimed is:

1. A portable, wearable ultrafiltration device comprising: a blood inlet for receiving blood flow from a patient;
    a pulsatile blood pump connected to the blood inlet, the pulsatile pump configured to pump blood from the patient in a pulsatile manner through the ultrafiltration device at a flow rate between 10 and 70 ml/min.;
    a blood filter for filtering excess body fluid from said blood, the blood filter including a filter inlet connected to the pulsatile blood pump and a fixed semiporous filter material having a first surface in contact with the patient's blood and a second surface on which fluid from the patient's blood is received, the pulsatile pump pumping the patient's blood to and through the filter with sufficient pressure to force fluid from the blood through the semiporous filter material, the blood filter having a blood side and a fluid side configured so that the only fluid on the fluid side of the blood filter is fluid separated from the blood passing through the blood side of the blood filter, the rate of fluid separation from the blood is configured to be adjusted by a combination of the flow rate being between 10 and 70 ml/min and by variably controlling a continuous fluid flow from the blood filter;
    a blood outlet connected to the blood filter, the blood outlet receiving blood from the blood filter and conducting the blood back to the patient; and
    a fluid bladder including a bladder inlet connected to the fluid side of the blood filter, the fluid bladder receiving and collecting fluid from the fluid side of the blood filter, the wearable ultrafiltration device constructed and configured to operate while in various three-dimensional orientations on the body of the patient.

2. The portable, wearable ultrafiltration device of claim 1 wherein the device weighs less than five (5) pounds.

3. The portable, wearable ultrafiltration device of claim 1 wherein the pulsatile pump pumps blood through the filter in a pulsed manner at a flow rate of between 15 and 200 ml/min.

4. The portable, wearable ultrafiltration device of claim 1, further comprising: an anticoagulant reservoir; and
    a first micropump for pumping anticoagulant from said anticoagulant reservoir into said blood at a location between said blood inlet and said blood filter.

5. The portable, wearable ultrafiltration device of claim 1, further comprising a microcontroller programmed to control said pulsatile pump flow rate and a variable continuous fluid flow from the blood filter.

6. The portable, wearable ultrafiltration device of claim 5, further comprising a moisture sensor inside a covering about said ultrafiltration device, said moisture sensor providing a moisture signal to said microcontroller when moisture is sensed inside said covering.

7. The portable, wearable ultrafiltration device of claim 6, wherein said microcontroller provides a signal that turns said pulsatile pump off after receiving said moisture signal when moisture is sensed inside said covering.

8. The portable, wearable ultrafiltration device of claim 5, further comprising a bladder sensor for sensing a fullness of said fluid bladder, said bladder sensor configured to provide a full signal to said microcontroller when said bladder sensor senses that said fluid bladder is full.

9. The portable, wearable ultrafiltration device of claim 5, further comprising a battery device configured to power the wearable ultrafiltration device continuously for at least six to twenty-four hours.

10. The portable, wearable ultrafiltration device of claim 1, wherein said fluid bladder contains an absorbent material that reduces the movement of the fluid within said fluid bladder.

11. A portable, wearable ultrafiltration device comprising: a blood inlet for receiving blood flow from a patient;
    a pulsatile pump connected to the blood inlet for pumping blood from the blood inlet to and through the ultrafiltration device, the pulsatile pump establishing an adjustable pulsed blood flow rate of between 10 and 200 ml/min;
    a blood filter for filtering an ultrafiltrate fluid from said blood, the blood filter including a filter inlet connected to the pulsatile blood pump and a fixed semiporous filter material having a first surface in contact with the patient's blood and a second surface on which ultrafiltrate fluid from the patient's blood is received, the pulsatile pump configured to pump the patient's blood through the filter with sufficient pressure to force excess body fluid from the blood through the semiporous filter material, the blood filter having a blood side and a fluid side configured such that the only fluid on the fluid side of the blood filter is ultrafiltrate fluid separated from the blood passing through the blood side of the blood filter, the rate of ultrafiltrate removal being both continuous and adjustable by a combination of varying the blood flow rate between 10 and 200 ml/min and by controlling a continuous and variable ultrafiltrate flow from said blood filter, a blood outlet for returning said blood to said patient; and a fluid reservoir configured to receive said ultrafiltrate fluid from said blood filter and for temporarily storing said ultrafiltrate fluid; said ultrafiltration device configured to operate while in various three-dimensional orientations.

12. The portable, wearable ultrafiltration device of claim 11 further comprising a pump having an inlet connected to the fluid side of the blood filter and an outlet connected to the fluid reservoir, the pump pumping ultrafiltrate fluid from the blood filter to the fluid reservoir.

13. The portable, wearable ultrafiltration device of claim 11 further comprising an anticoagulant reservoir; and a micropump, the micropump pumping anticoagulant from said anticoagulant reservoir into the blood before the blood enters the blood filter.

14. The portable, wearable ultrafiltration device of claim 13 wherein the micropump pumps anticoagulant from the anticoagulant reservoir into the blood at a location between said blood pump and the blood filter.

15. The portable, wearable ultrafiltration device of claim 11 wherein the blood filter comprises a plurality of miniaturized blood filters connected in series.

16. The portable, wearable ultrafiltration device of claim 11 wherein the blood filter comprises a plurality of miniaturized blood filters connected in parallel.

17. The portable, wearable ultrafiltration device of claim 11 wherein the pulsatile pump further comprises a double channel pulsatile pump.

18. A portable, wearable ultrafiltration device comprising:

a blood inlet for receiving blood flow from a patient;

a battery device powered pulsatile blood pump connected to the blood inlet such that blood from the patient is pumped by the pulsatile pump through said ultrafiltration device;

a blood filter for filtering overload body fluid from said blood, the blood filter including a blood side and a fluid side, the blood side having a blood filter inlet connected to the pulsatile blood pump and a blood filter outlet, the fluid side having a fluid outlet, the blood filter further comprising a fixed semiporous filter material having a first surface on the blood side of the blood filter in contact with the patient's blood and a second surface on the fluid side on which overload body fluid from the patient's blood is received, the pulsatile pump configured to pump the patient's blood through the filter with sufficient pressure to force overload body fluid from the blood through the semiporous filter material, the fluid side configured with no fluid inlet such that the only fluid on the fluid side of the blood filter is the overload body fluid separated from the blood that passes from the blood side of the blood filter to the fluid side of the filter through the semiporous filter material;

the blood filter outlet receiving blood from the blood filter and conducting the blood back to the patient; and a fluid reservoir including a reservoir inlet connected to the blood filter and configured to receive the overload body fluid separated from the patient's blood, said overload body fluid being removed from the patient's blood at a continuous and an adjustable rate that can be varied by a combination of varying a pumping rate of the battery powered pulsatile pump and variably occluding a continuous overload body fluid flow from being received by the fluid reservoir; the wearable ultrafiltration device being configured to operate while in various three-dimensional orientations while being completely worn on the body of the patient.

19. The portable, wearable ultrafiltration device of claim 18 wherein the semiporous filter material comprises a plurality of hollow fibers having fixed ends.

* * * * *